United States Patent
Lewis (10) Patent No.: US 8,931,905 B2
(45) Date of Patent: Jan. 13, 2015

(54) BINOCULAR MEASUREMENT METHOD AND DEVICE

(71) Applicant: James Waller Lambuth Lewis, Tullahoma, TN (US)

(72) Inventor: James Waller Lambuth Lewis, Tullahoma, TN (US)

(*) Notice: Subject to any disclaimer, the term of this patent is extended or adjusted under 35 U.S.C. 154(b) by 0 days.

(21) Appl. No.: 13/750,929

(22) Filed: Jan. 25, 2013

(65) Prior Publication Data

US 2014/0211167 A1    Jul. 31, 2014

(51) Int. Cl.
*A61B 3/00* (2006.01)
*A61B 3/14* (2006.01)

(52) U.S. Cl.
USPC .......................................... 351/246; 351/209

(58) Field of Classification Search
USPC ................................. 351/200–246
See application file for complete search history.

(56) References Cited

U.S. PATENT DOCUMENTS

| | | | |
|---|---|---|---|
| 5,963,300 A * | 10/1999 | Horwitz ........................ | 351/209 |
| 7,427,135 B2 | 9/2008 | Chen et al. | |
| 7,878,652 B2 | 2/2011 | Chen et al. | |
| 8,668,337 B2 * | 3/2014 | Waldorf et al. ............... | 351/209 |
| 2011/0157550 A1 | 6/2011 | Chen et al. | |
| 2013/0162640 A1 * | 6/2013 | Kim et al. ..................... | 345/419 |

FOREIGN PATENT DOCUMENTS

WO  PCT/US2012/023097    1/2012

* cited by examiner

*Primary Examiner* — Mohammed Hasan
(74) *Attorney, Agent, or Firm* — Hornkohl Intellectual Property Law, PLLC; Jason L. Hornkohl (57) ABSTRACT

A method of performing an ophthalmic test on an examinee's eyes utilizes a three-dimensional display screen that includes a right-eye image and a left-eye image to induce ocular responses in the examinee's eyes. The right and left-eye images are varied while detection devices are used to monitor the examinee's eyes ocular responses to the variations. The induced ocular responses of the examinee's eyes are then used to diagnose any ocular, mental or neurological conditions present. The ocular response inducing images are preferably included in a three-dimensional video game such that a players' performance while playing the game will be indicative of any disorders that may be present.

20 Claims, 7 Drawing Sheets

Example: Attractive 2-D or 3-D display controls gaze and focus of examinee for optimal detection condition, relaxed or intended focus. 3-D display controls the ocular convergence.

BINOCULAR MEASUREMENT METHOD AND DEVICE

This is a Utility Patent Application filed for the invention by James Waller Lambuth Lewis for a "Binocular Measurement. Method and Device" that claims priority from U.S. Provisional Patent Application Ser. No. 61/590,338 filed Jan. 25, 2012.

BACKGROUND OF THE INVENTION

1. Field of the Invention

The present disclosure is generally related to medical measurements and, more particularly, is related to the objective methods for achieving ophthalmic diagnostics or ocular, physical, or mental status detection that is especially friendly far children.

2. Description of the Prior Art

Traditional ophthalmic tests such as the Swinging Flashlight Test, Cover Uncover Test, Red Reflex Test, Bruckner Test, and illumination Test are typically performed using basic instruments such a light or cover that are held by an examiner and positioned in front of the eyes of an examinee. Ophthalmic measurements using more advanced devices normally rely on a fixation chin rest, head rest, and subjective response or cooperation. Unfortunately, these tests require the participation of the examiner and alignment or cooperation of the examinee and are often considered difficult especially for the pre-school or pre-verbal children. In addition, the eyes are not always in a constant condition during a measurement. Repeatable ophthalmic tests depend on reasonably stable gaze, convergence, accommodation, pupil size, and tear film, condition. Consider the refraction test for example: the degree of near- or farsightedness depends on the relaxation of lens and the pupil size, which varies with the level of illumination. To obtain dependable refraction measurement, the illumination level and the relaxation of accommodation must be adequate.

Therefore, what is needed are improved, methods to provide or induce adequate ocular conditions for performing traditional and non-traditional ophthalmic or ocular tests.

BRIEF SUMMARY OF THE INVENTION

The present invention is directed toward a method of performing a binocular ophthalmic measurement on an examinee's eyes. A preferred embodiment utilizes a three-dimensional display screen that includes at least two component display ages that are independently delivered to the eyes of a viewer such that each eye receives only one of the display images while the traditional or non-traditional ocular measurements are performed at the same time. The present invention can use any of the many types of three-dimensional display technology so long as the display includes at least two component images that are delivered independently to the eyes of a viewer.

The method begins with the positioning of the examinee in front of the display screen. First and second display images are produced on the three-dimensional screen that induce desired ocular responses in the examinee's eyes. The ocular responses of the examinee's eyes are measured by an ocular signal detector that diagnoses ocular conditions of the examinee's eyes. The ophthalmic measurements are performed simultaneously and binocularly with the ocular responses of the examinee's eyes to diagnose the ocular, physical condition or mental status of the examinee. The ocular response induced by the three dimensional stimuli can include a gaze direction, binocular convergence, accommodation, refractive error, pupil contraction and dilation response of the examinee's eyes. The ocular response also includes the speed, the latency, and the amplitude of the eyeballs', pupils', and lenses', movements related to the visual stimuli. The measurements can utilize infrared radiation/detection that minimizes discomfort and prevents interference of the 3D stimuli viewing. The optical measurements can also use additional visible light sources or directly use the visible light signal that is result from the 3-dimensional viewing stimuli.

The ophthalmic measurement and the measurements of the ocular response of the examinee's eyes are used to diagnose any ocular conditions present in the examinee's eyes such as a refractive error, a cataract, an optical opacity, tear film condition, and/or an ocular aberration and to do so with the knowledge of the gaze, convergence, accommodation, pupil response, duration of focus or attention, etc. Abnormalities in eye functions may also signal serious and potentially fatal diseases, neurological, psychological, and behavioral disorders, and learning disabilities. For instance, abnormal pupil response, uncharacteristic saccades, and inability of performing smooth rapid pursuit may be indicatory signals to attention. deficit hyperactivity disorder (ADHD), dyslexia, autism, post-traumatic stress disorder (PTSD), etc., Examining eyes, particularly at a young age, can reveal clues about underlying conditions before they become difficult, to cure or grave problems.

As an example, a cover-uncover test or an alternative-cover test is preferably performed by alternately presenting an image to each of the examinee's eyes and to both of the examinee's eyes in the timely manner of the clinical tests while the gaze directions of the eyes are recorded. A swinging-flashlight test is performed by altering an illumination level of the left-eye display image with respect to the right-eye display image while both eyes' pupil movements are registered. The tests are preferably included in an interactive video produced on the display screen with images that induce an ocular response in the examinee and respond to inputs from the examinee.

Another embodiment of the present invention is directed toward a method of performing an ophthalmic test on an examinee using a three-dimensional display screen. The method begins with positioning the examinee in front of the three-dimensional display screen. The examinee is then provided a game controller, and the examinee is prompted to play a three-dimensional video game. An ocular performance of the examinee's eyes is monitored while the examinee plays the three-dimensional video-game. A camera is preferably used to perform photorefraction and capture images of the examinee's eyes. The three-dimensional video game includes images designed to implement: an ophthalmic test and to induce an ocular response in the examinee's eyes. A visible or infrared video camera is used to perform dynamic photon and capture video images of the examinee's eyes. The ophthalmic tests preferably include a cover-uncover test, disappearing image test, binocular refraction test, light reflex (Bruckner) test, binocular visual acuity test, and illumination test.

DETAILED DESCRIPTION OF THE INVENTION

Figure 1:
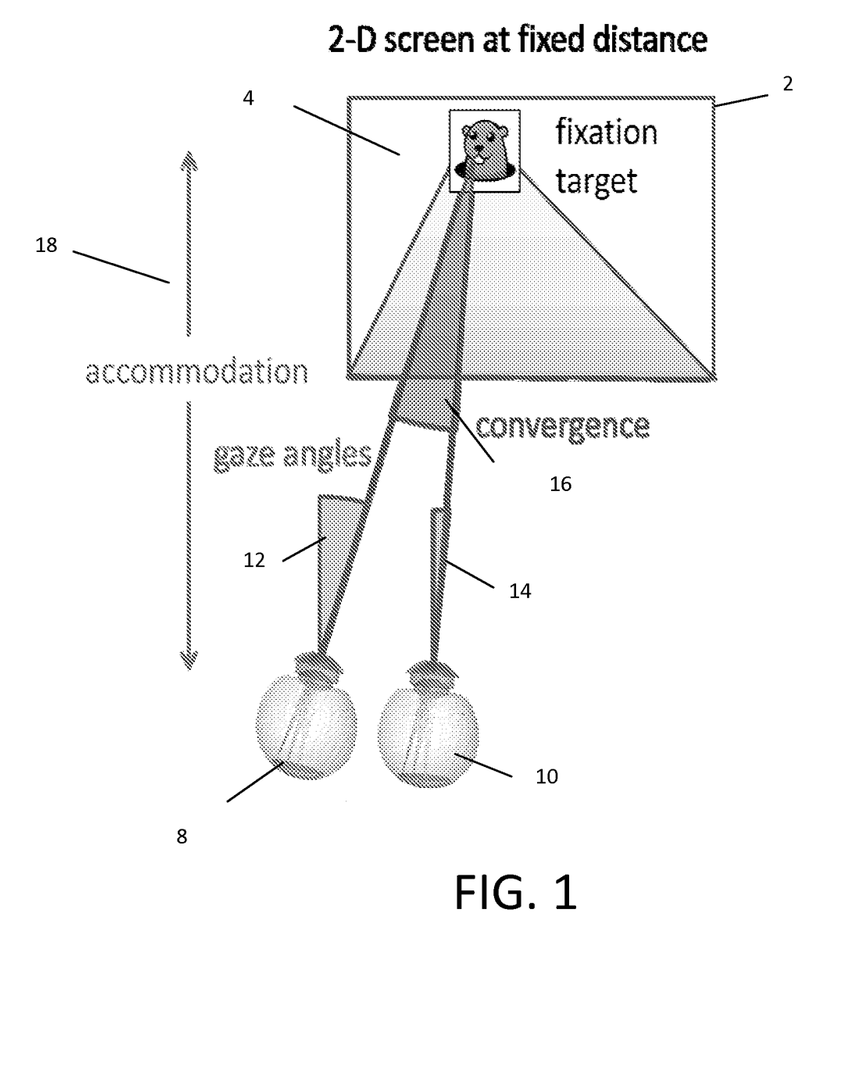
FIG. 1 is an illustration demonstrating the viewing of a two-dimensional display screen.

Referring now to FIG. 1, an illustration that depicts the viewing of a two-dimensional display screen is shown. A two-dimensional screen 2 displays at two-dimensional image 4 at a fixed distance from the eyes 8 and 10 of a viewer. While watching a two-dimensional video, the viewer's eyes 8 and 10 must fix or lock on a particular point on the two-dimensional image 4 at any given time. Therefore, the gazing angles 12 and 14, convergence 16, and the crystalline lens accommodation 18 or refraction of the eyes of both eyes are demanded by the two-dimensional image 4 at the instance. This demand is even more intense when the viewer is playing a video game.

By monitoring the eyes of an examinee while the examinee plays a video game designed to test various ocular properties and conditions, standard ophthalmic tests can be performed in a less intrusive and more entertaining manner. The level of the demands placed on the examinee's eyes and the response of the examinee's eyes to the demands can be examined through their performance or score while game playing if the performance of both eyes is detected and monitored simultaneously, the ocular assessment is enhanced to a higher level with the additional known conditions, i.e. the gaze angles 12 and 14, convergence 16, accommodation 18.

Figure 2:
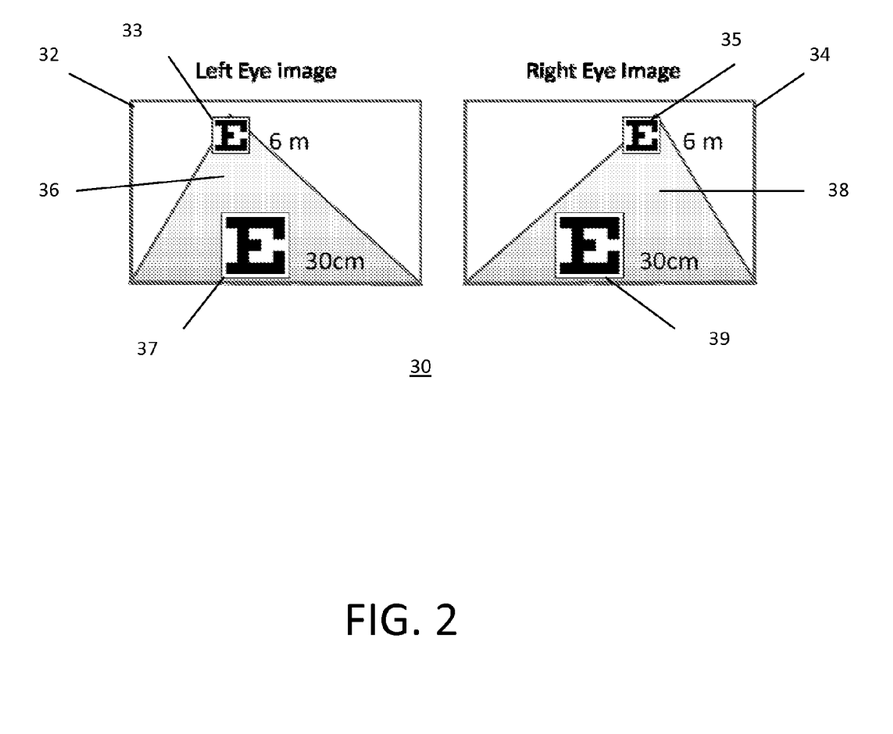
FIG. 2 is an illustration demonstrating the use of a three-dimensional display screen having left and right eye images in accordance with an embodiment of the present invention.

Referring now to FIG. 2, an illustration is shown that demonstrates the use of a three-dimensional display screen having left and right eye images in accordance with an embodiment of the present invention. A three-dimensional screen 30, in contrast to a two-dimensional screen, displays two independent eye images 32 and 34, where each image reaches only one of the two eyes of a viewer, at a fixed distance from a viewer. If the viewer has healthy binocular viewing, the gaze angles 36 and 38 of both eyes are aligned to the fixation targets 40 and 42 and the two retinal images are fused in the viewer's brain. The gaze angles and convergence are demanded by the two projected images 32 and 34 or targets present in the images 32 and 34. The accommodations of both eyes, however, are affected by the convergence. As shown in FIG. 2, both images 32 and 34 are received by the eyes at the same instant. When the images 32 and 34 are fused in the brain, the target small E's 33 and 35 at the upper portion of the images demand a smaller convergence than the large E's 37 and 39. The retinal disparity drives the crystalline lens to relax the accommodation when gazing at small E. As a result, the viewer sees and believes the smaller E is located at a farther distance behind the screen.

The present invention uses three-dimensional display technology to control a viewer's accommodation similar to having the viewer looking at the letter chart at from different distances. The viewer's response to the stimuli can then be monitored in any of a number of established ways to detect ocular conditions in the viewer's eyes. For example, a binocular refraction test can be performed in accordance with the present invention by utilizing three-dimensional stimuli or targets 33, 35, 37 and 39 positioned at different distances to relax children's accommodation. Refraction measurements made while examinee's are viewing subjects positioned in the component images of the three-dimensional images projected at near, mid-range, and far distances can be indicative of a number of ocular conditions.

The binocular refraction test might be preferably implemented through cartoon backgrounds set at a normal daylight level so that children's eyes are in the normal daytime viewing status. Scenery may be used if desired. Cartoon characters, such as a teddy bear, an eye doctor, or a fur-ball, etc., are presented as moving from a near to far distance (≥6 meters or 20 feet) to induce various levels of crystalline lens accommodation/relaxation. In the case of the small percentage of the population without stereo vision, both binocular depth cue (stereopsis, convergence, shadow stereopsis) and monocular depth cue (size proportion, visual angle, occlusion, aerial perspective, lighting/shading) may be applied to design the fixation targets. A system such as an infrared adaptive photoscreening system or an autorefractor is preferably used to rapidly record binocular refraction at desired ocular stimulation. Design parameters such as size, resolution or blurriness and contrast etc. are incorporated into each cartoon program to induce various ocular relaxation and accommodation conditions. To ensure patient comfort, and to prevent the uncoupling of vergence and accommodation, these design parameters will preferably evoke appropriate pupil sizes for sufficiently long focus depth to allow accurate optical measurements to be taken.

Figure 3:
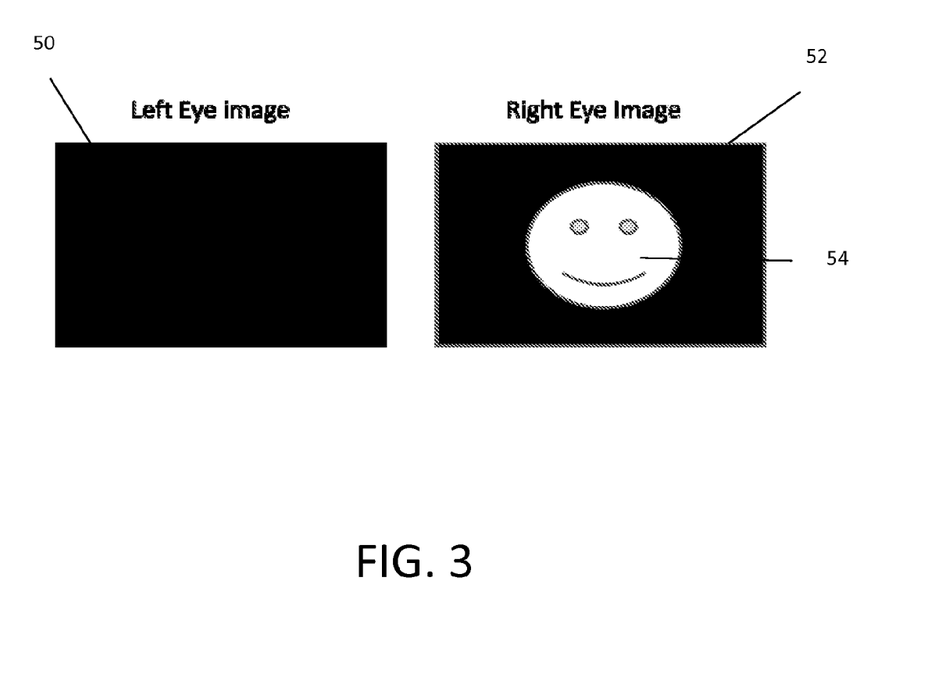
FIG. 3 is an illustration of three-dimensional imagery for use in performing a swinging-flashlight ophthalmic test in accordance with an embodiment of the present invention.

Referring now to FIG. 3, an illustration of three-dimensional imagery for use in performing a swinging-flashlight test in accordance with an embodiment of the present invention is shown. The present invention utilizes three-dimensional display technology to perform automatic pupil testing, similar to the clinical Swinging Flashlight Test. The left- and right-eye images 50 and 52 are used to create testing conditions similar to the clinical "swinging flashlight test" whereby a pencil light is used to alternately illuminate the pupils of an examine. This can be accomplished by using the two images 50 and 52 present in a three-dimensional vision display to alternately display a target 54 and illuminate the eyes of an examinee instead of displaying of a three-dimensional image in the conventional manner. The background is preferably very dark to enable examination of naturally dilated pupils. As the dark-adapted pupils stabilize, an image on the screen will suddenly be shown that includes bright white light illuminating both eyes or only a selected eye. The display then returns to the dark screen. The light-dark durations are preferably comparable to the light-dark durations of the clinical swinging-light test and both pupils' responses are continuously recorded.

Figure 4:
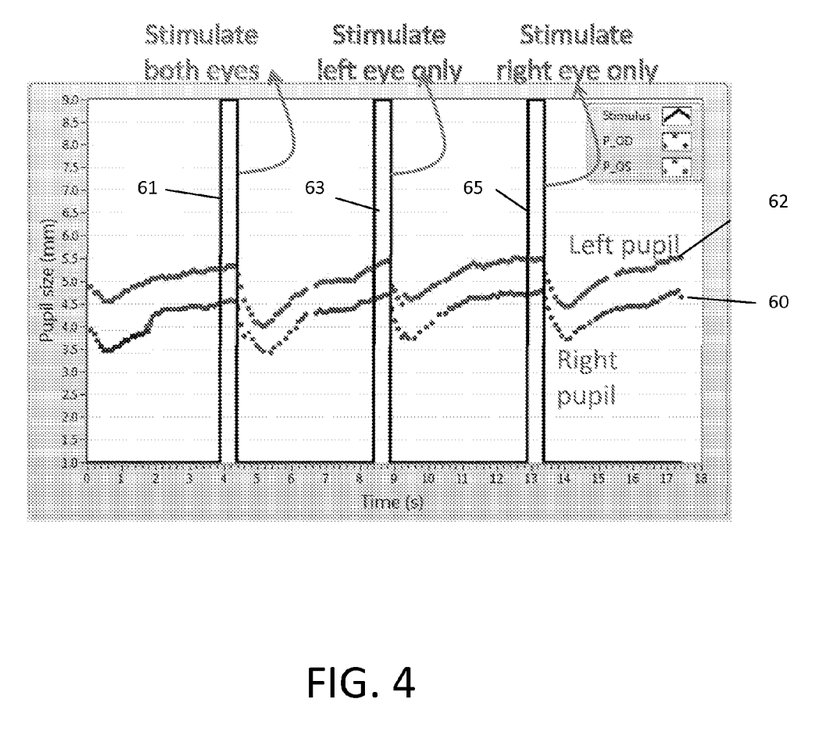
FIG. 4 is a graph illustrating pupil size changes in an examine's eye in response to a three-dimensional illumination test that is performed in accordance with an embodiment of the present invention.

FIG. 4 is a graph illustrating pupil size changes in an examinee's eye in response to a three-dimensional illumination test as illustrated in FIG. 3 in accordance with an embodiment of the present invention. The plot shows changes in the right 60 and left 62 pupil sizes over time of a patient viewing a three-dimensional display operating in accordance with the present invention. The three spikes 61 and 63 and 65 indicate the times when target smiley face were illuminating both of the examinee's eyes (OU) 61, the right eye only (OD) 65, and the left eye only (OS) 63. In between the spikes 61, 63 and 65, both images to the eyes are completely black, thereby inducing the pupil to naturally dilate. The two pupil contraction responses 60 and 62 shown in the plot have diagnostic implications regarding of the neural health condition of the eyes. The latency and stability of the examinee's pupil response to the monocular illumination is potentially indicative of the examinee's neurological health condition, autism and other mental conditions.

Figure 5:
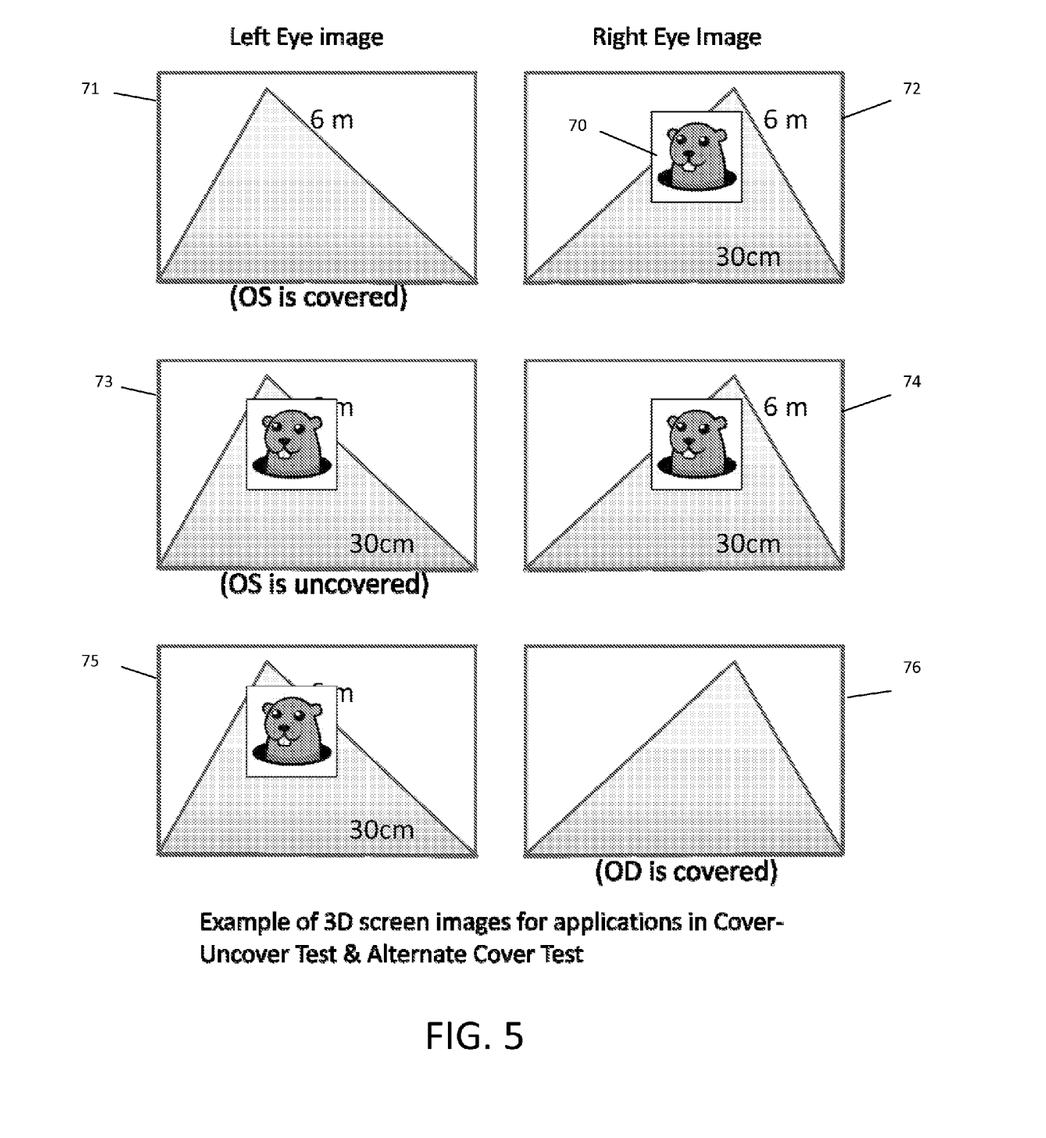
FIG. 5 is an illustration of a method of performing a Cover-Uncover ophthalmic test with a three-dimensional display in accordance with an embodiment of the present invention.

FIG. 5 is an illustration of a method of performing a cover-uncover or corneal reflex ophthalmic test with a three-dimensional display in accordance with an embodiment of the present invention. The method is a substitute for a traditional cover-uncover test that uses three-dimensional display technology. The cover-uncover test is a standard clinical test that is used to identify strabismus (phoria and tropia). The present invention utilizes a three-dimensional display as a tool to show the target 70 (at both near and far) without using an occluder. As shown in the pictures 71-76, the fixation target 70 can vanish in one of the right or left eye images that make up a three-dimensional display similar to the blocking of one eye's view as performed in the traditional cover-uncover clinical testing. If both eyes of the viewer are healthy and their binocular vision is not impaired, the viewer will not experience interruption of the video during its viewing. This method is much more comfortable and relaxing, especially for young children, than the traditional test. If the binocular vision of the viewer is impaired, he/she will be required to adjust their gaze or will experience viewing difficulties when one or the other target displayed on the two images of the three-dimensional display vanishes. Thus, a three-dimensional screen, can be used to perform an oplithahnic test using the techniques of the present invention.

Professional skill is required to swiftly and properly disturb a child's normal "binocular viewing" to expose hidden ocular abnormalities. Performing the cover-uncover test with three-dimensional display technology provides a tool to introduce the required viewing disturbance without the need of a clinician. The three-dimensional screen projects the same, or different, fixation targets to the eyes with and without using an occluder. The fixation target can vanish in one eye's visual field which is similar to covering one eye in clinical testing.

A cartoon fixation target is preferably presented or occluded during a cartoon to mimic the standard cover-uncover and alternate-cover tests. This method, especially for young children, is more comfortable and relaxed than being tested by an adult using his/her thumb or an occluder. An adaptive photoscreening system may be used to detect ocular orientations, and motility may be calculated from the Hirschberg Corneal reflex-shift that is time-synchronized with the cartoon.

Figure 6:
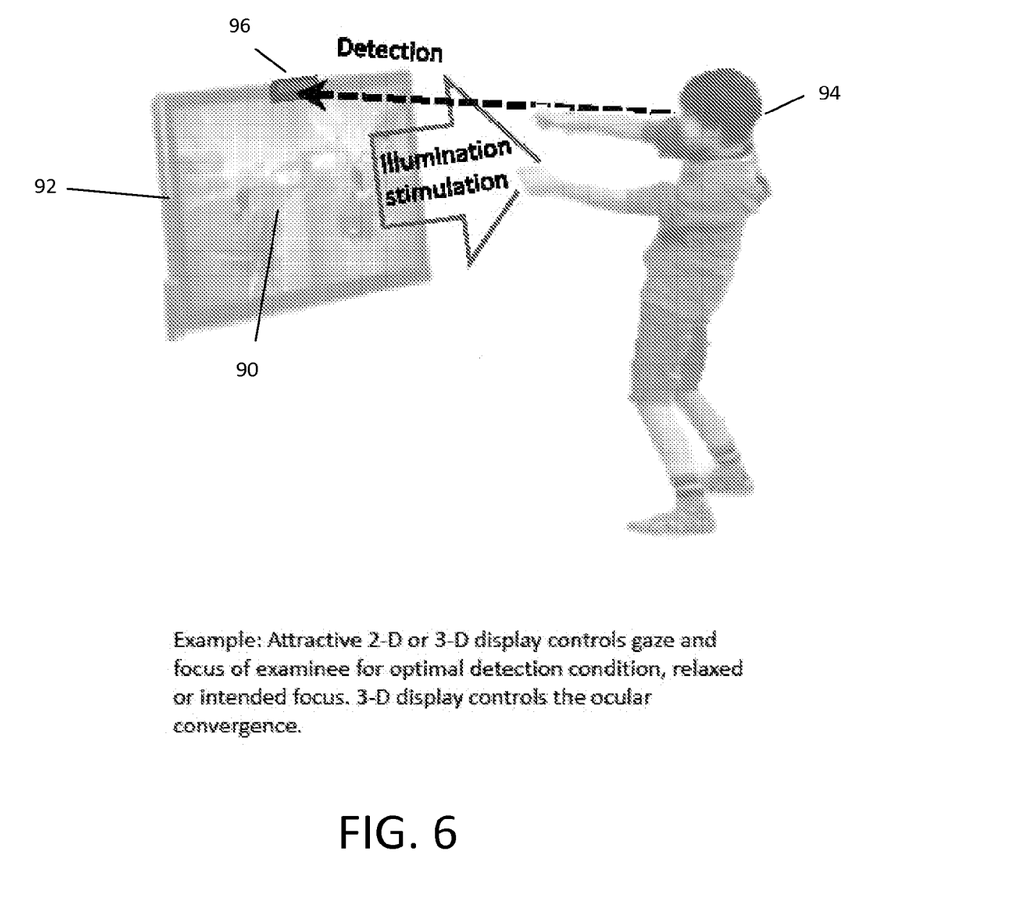
FIG. 6 is an illustration of the implementation of an embodiment of the present invention using a contemporary gaming setup.

The ophthalmic testing examples described above and the demands for desired ocular cooperation (gaze, convergence, accommodation status) and illuminating conditions can be incorporated into, and accommodated precisely by, the two-dimensional and three-dimensional technology available in a contemporary video game playing set-up. Referring now to FIG. 6, a drawing is shown that illustrates implementation of the present ophthalmic methods using a contemporary gaming setup. The visual stimulus in the form of a video game 90 is projected onto a three-dimensional display 92. The examinee's attraction to the video game 90 is used to control the gaze and focus of the examinee 94. The various ophthalmic tests are performed with the images used to create the game play. If the examinee 94 suffers from an ophthalmic condition, it will be reflected in their game play. For example, an inability to see a warning sign, displayed in only of the two images used to produce the three-dimensional display 92, may induce a player to run off the road in a driving game in addition, the examinee's eyes are monitored by ocular detection devices 96 during the game play to detect any ocular conditions induced by the testing embedded in the game play.

Figure 7:
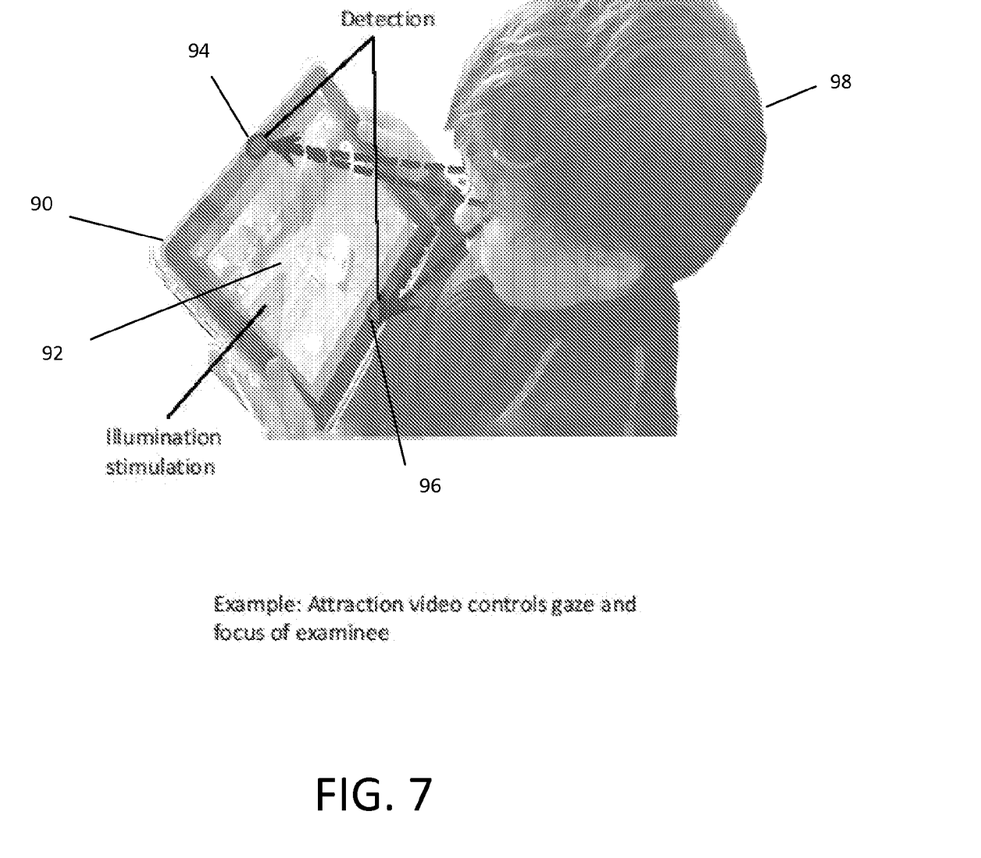
FIG. 7 is an illustration of a method of implementing an ophthalmic test using a modern mobile device in accordance with an embodiment of the present invention.

As shown in FIG. 7, the present invention can be easily implemented on a modern mobile device 90 by using the display 92 of the device to produce the required images to perform the ophthalmic tests on the viewer 98 and using the device's cameras 94 and 98 to detect changes in the optic properties of the viewer's eyes and their gaze and locus.

It is to be understood that the present invention is not explicitly limited to the embodiments illustrated in the detailed description given above. Various changes and modifications may be made to the methods and ophthalmic test setups described herein without departing from the spirit and scope of the invention as defined in the following claims.

What is claimed is:

1. A method of performing an improved ophthalmic measurement on an examine, said method comprising the steps of:
    positioning said examinee in front of a single display;
    utilizing said single display to independently produce a right-eye image that is only visible to a right eye of said examinee and a left-eye image that is only visible to a left eye of said examinee;
    producing visual stimuli in said right-eye image and said left-eye image that induce an ocular response in said examinee's eyes; and
    simultaneously measuring an ocular condition of said examinee's eyes to diagnose a condition of said examinee.

2. The method of claim 1 wherein said single display is a three-dimensional display screen, a headset display, or a holographic display and said left-eye image and said right-eye image are component images of a three dimensional image produced by said three-dimensional display, said headset display, or said holographic display.

3. The method of claim 1 wherein said step of simultaneously measuring an ocular condition of said examinee's eyes further comprises measuring a gaze direction or pupil response of said examinee's eyes.

4. The method of claim 1 wherein said step of simultaneously measuring an ocular condition of said examinee's eyes further comprises measuring a binocular convergence of said examinee's eyes induced by said single display displaying different right-eye and left-eye images.

5. The method of claim 1 wherein said step of simultaneously measuring an ocular condition of said examinees eyes further comprises measuring an accommodation of said examinee's eyes.

6. The method of claim 1 further comprising the step of performing optical measurements while illuminating said examinee's eyes with infrared radiation.

7. The method of claim 1 wherein said step of simultaneously measuring said ocular condition of said examinee's eyes to diagnose a condition of said examinee further comprises diagnosing at least one of a refractive error, a cataract, an optical opacity, a tear film condition, and an ocular aberration.

8. The method of claim 1 wherein the step of producing visual stimuli in said right-eye age and said left-eye image further comprises the step of alternately presenting an in age to each eye of said examinee's eyes and to both of said examinee's eyes.

9. The method of claim 1 wherein the step of producing visual stimuli in said right-eye image and said left-eye image further comprises the step of altering an illumination level of said left-eye image with respect to said right-eye image to evaluate an ocular condition of said examinee's eyes.

10. The method of claim 1 further comprising the step of producing an interactive three-dimensional video on said single display with images that induce an ocular response in said examinee and recording said examinee's reactions to said interactive three-dimensional video.

11. The method of claim 1 wherein said condition further comprises a mental or psychological status of said examinee based upon said ocular response.

12. A method of performing an ophthalmic test, said method comprising:
   using a three-dimensional display to produce a three-dimensional image that includes an independent right-eye image and an independent left-eye image;
   varying an illumination or contrast level between said independent right-eye image and said independent left-eye image; and
   monitoring an ocular response of an examinee's eyes to said varying of said illumination or contrast level between said independent right-eye image and said independent left-eye image to determine an ocular condition of said examinee's eyes.

13. The method of claim 12 comprising the steps of alternately displaying an image of a subject in said independent right-eye image, said independent left-eye image and both said independent right and independent left-eye images and monitoring an ocular response of said examinee's eyes induced by said alternately displaying of said image of said subject to determine an ocular condition of said examinee's eyes.

14. The method of claim 12 wherein monitoring an ocular response further comprises detecting an accommodation and refractive error for said examinee's eyes.

15. The method of claim 12 wherein monitoring an ocular response further comprises detecting a gaze angle for said examinee's eyes.

16. The method of claim 12 wherein monitoring an ocular response further comprises detecting a contraction and dilation response for said examinee's eyes.

17. The method of claim 12 wherein monitoring an ocular response further comprises producing a retinal reflex image for said examinee's eyes.

18. A method of performing an ophthalmic test on an examinee using a three-dimensional display, said method comprising the steps of:
   positioning said examinee in front of said three-dimensional display;
   providing a game controller or a microphone to said examinee;
   prompting said examinee to play a three-dimensional video game; and
   monitoring an ocular performance of said examinee's eyes while said examinee plays said three dimensional videogame;
   wherein said three-dimensional video game includes images designed to implement an ophthalmic test and induce an ocular response in said examinee's eyes.

19. The method of claim 18 further comprising the step of using a video camera to perform dynamic photorefraction and capture video images of said examinee's eyes.

20. The method of claim 18 wherein said ophthalmic test includes at least one of a cover-uncover test, disappearing image test or illumination test.

* * * * *